(12) United States Patent
Slattery et al.

(10) Patent No.: US 9,468,548 B2
(45) Date of Patent: Oct. 18, 2016

(54) SYSTEMS AND METHODS FOR DELIVERING A STENT TO A BODY LUMEN

(75) Inventors: David Slattery, Co Galway (IE); Michael Gilmore, Co Galway (IE); Aemon Curley, Co Galway (IE); Damian Kelly, Co Galway (IE)

(73) Assignee: CAPPELLA, INC., Westford, MA (US)

( * ) Notice: Subject to any disclaimer, the term of this patent is extended or adjusted under 35 U.S.C. 154(b) by 773 days.

(21) Appl. No.: 13/639,100

(22) PCT Filed: Apr. 4, 2011

(86) PCT No.: PCT/US2011/031085
§ 371 (c)(1),
(2), (4) Date: May 17, 2013

(87) PCT Pub. No.: WO2011/123852
PCT Pub. Date: Oct. 6, 2011

(65) Prior Publication Data
US 2013/0226279 A1    Aug. 29, 2013

Related U.S. Application Data

(60) Provisional application No. 61/320,690, filed on Apr. 2, 2010.

(51) Int. Cl.
*A61F 2/97* (2013.01)
*A61F 2/958* (2013.01)

(52) U.S. Cl.
CPC ................ *A61F 2/97* (2013.01); *A61F 2/958* (2013.01); *A61F 2002/9583* (2013.01)

(58) Field of Classification Search
CPC ............. A61F 2/95; A61F 2/954; A61F 2/97
USPC .............................................. 623/1.11, 1.12
See application file for complete search history.

(56) References Cited

U.S. PATENT DOCUMENTS

| 7,862,601 B2 * | 1/2011 | Sanati et al. ................. 623/1.11 |
| 2002/0049489 A1 * | 4/2002 | Herweck et al. ............ 623/1.13 |
| 2002/0099431 A1 * | 7/2002 | Armstrong et al. ......... 623/1.11 |
| 2009/0259286 A1 | 10/2009 | Ohri et al. |

FOREIGN PATENT DOCUMENTS

| EP | 1 649 829 A1 | 4/2006 |
| WO | 01/97715 A1 | 12/2001 |

\* cited by examiner

*Primary Examiner* — Kathleen Holwerda
(74) *Attorney, Agent, or Firm* — Oliff PLC

(57) ABSTRACT

A stent delivery system configured to deliver a stent to a target region of a body lumen may include a catheter; a stent associated with the catheter, the stent having a first region and a second region; a balloon associated with the catheter, the balloon having a first balloon portion associated with the catheter proximate the first region of the stent and a second balloon portion associated with the catheter proximate the second region of the stent; and a sheath about the stent and the balloon, the sheath maintaining the stent in an undeployed configuration for delivery to a target region of a body lumen. The sheath may comprise a first sheath region configured to split at a first pressure thereby permitting the first region of the stent to assume a deployed configuration, a second sheath region configured to split at a second pressure thereby permitting the second region of the stent to assume a deployed configuration, the second pressure being greater than the first pressure and the first pressure being insufficient to cause the second region of the sheath to split, a split-stopping structure between the first and second sheath regions, the split-stopping structure being configured to prevent a split from propagating from the first sheath region to the second sheath region at the first pressure.

29 Claims, 4 Drawing Sheets

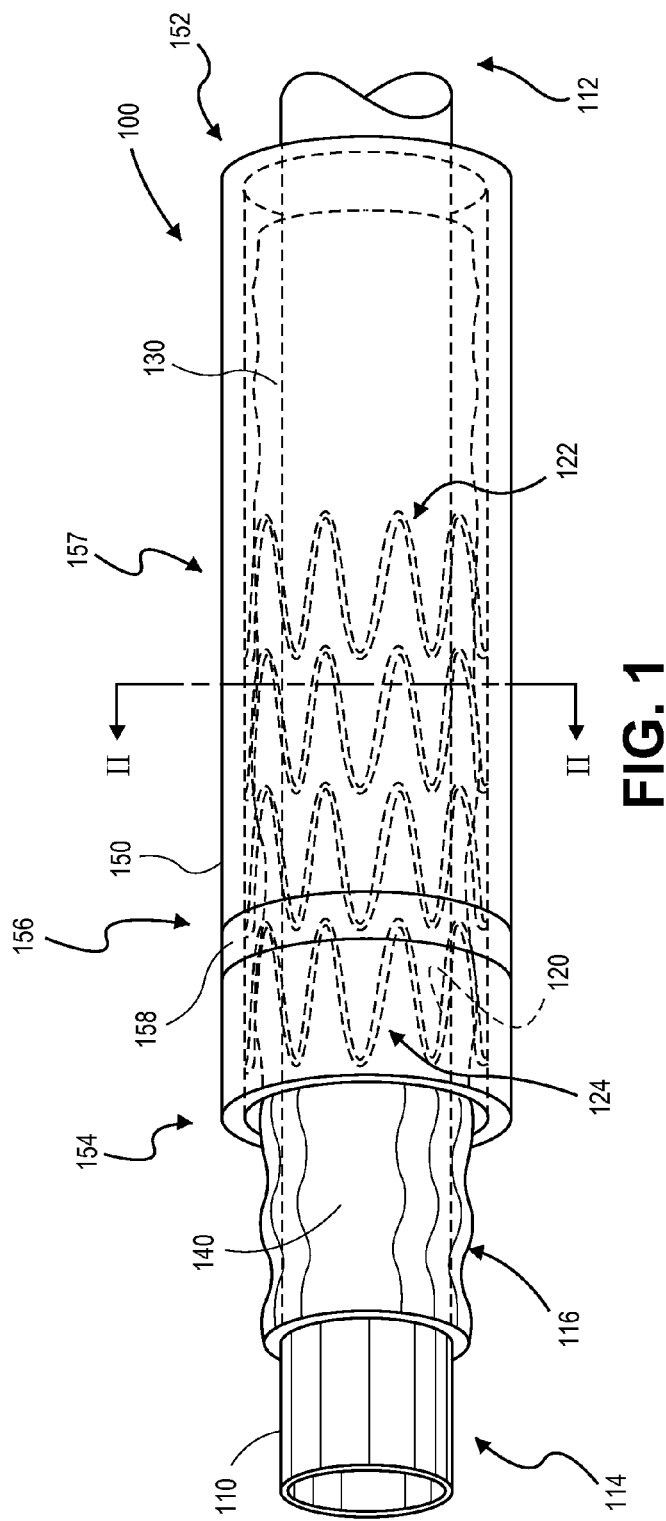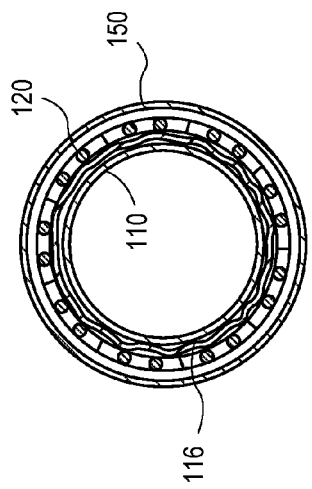

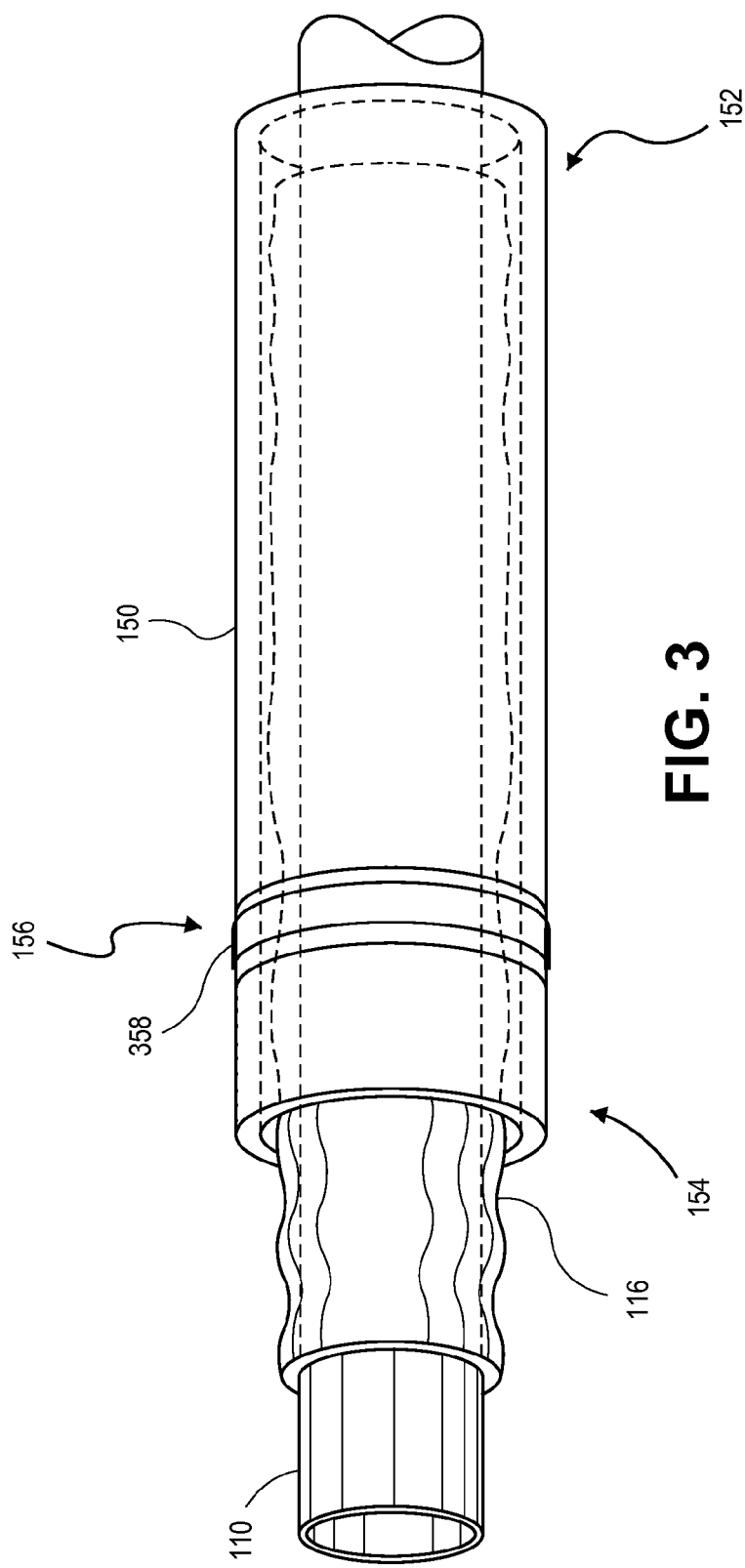

SYSTEMS AND METHODS FOR DELIVERING A STENT TO A BODY LUMEN

CROSS-REFERENCE TO RELATED APPLICATION

This application is filed under 35 U.S.C. 371 as a U.S. national phase application of PCT/US2011/031085, having an international filing date of Apr. 4, 2011, which claims priority to U.S. Provisional Patent Application No. 61/320, 690, having a filing date of Apr. 2, 2010, which is hereby incorporated by reference.

TECHNICAL FIELD

The present disclosure relates to systems and methods for delivering a stent to a body lumen.

BACKGROUND

Tubular prostheses typically fall into two general categories of construction. The first category of prosthesis is expandable upon application of a controlled force, often through the inflation of the balloon portion of a dilatation catheter, which expands the compressed prosthesis to a larger diameter to be left in place within a vessel, e.g., an artery, at the target site. The second category of prosthesis is a self-expanding prosthesis formed from, for example, shape memory metals or super-elastic Nickel-Titanium (NiTi) alloys, that will automatically expand from a compressed state when the prosthesis is advanced out of the distal end of the delivery catheter into the blood vessel.

Some known prosthesis delivery systems for implanting self-expanding stents include an inner lumen upon which the compressed or collapsed prosthesis is mounted and an outer restraining sheath that is initially placed over the compressed prosthesis prior to deployment. When the prosthesis is to be deployed in the body vessel, the outer sheath is moved in relation to the inner lumen to "uncover" the compressed prosthesis, allowing the prosthesis to move to its expanded condition. Some delivery systems utilize a "push-pull" design and technique in which the outer sheath is retracted while the inner lumen is pushed forward. Still other systems use an actuating wire that is attached to the outer sheath. When the actuating wire is pulled to retract the outer sheath and deploy the prosthesis, the inner lumen must remain stationary, to prevent the prosthesis from moving axially within the body vessel.

There have been, however, problems associated with these delivery systems. Systems that use the "push-pull" design can experience movement of the collapsed prosthesis within the body vessel when the inner lumen is pushed forward. This movement can lead to inaccurate positioning and, in some instances, possible perforation of the vessel wall by a protruding end of the prosthesis. Further, systems that utilize the actuating wire design will tend to move to follow the radius of curvature when placed in curved anatomy of the patient. As the wire is actuated, tension in the delivery system can cause the system to straighten. As the system straightens, the position of the prosthesis changes because the length of the catheter no longer conforms to the curvature of the anatomy. This change of the geometry of the system within the anatomy also leads to inaccurate prosthesis positioning.

Systems are known for delivering or implanting a self-expanding device in a vessel by operation of a balloon to rupture a sheath that holds the self-expanding device in a compressed state. When the device is located at the desired position in the vessel, the balloon is inflated, rupturing the sheath, thereby allowing the device to expand into position. Examples of these systems include U.S. Pat. No. 6,656,213 to Solem and U.S. Pat. No. 5,549,635 to Solar. However, in these fast rupture systems, there is no opportunity to readjust the position of the stent to correct for misalignment or misplacement.

While Solem '213 and Solar '635 describe systems for delivering a self-expanding stent by operation of a balloon to rupture a sheath, experimental implementations of these types of systems have shown results that fall short of expectations. In experiments on porcine coronary arteries, the stent misalignment from the target implant position was in the range of 3-10 mm, which is suboptimal for the treatment of vascular lesions and, in particular, bifurcation lesions.

There are two primary structural factors that lead to stent misplacement for these systems: firstly, slight movements of the delivery system due to patient movement and/or delivery system movement between positioning and deploying the device; and secondly, foreshortened views of the lesion and delivery system. The inability of these systems to offer accurate placement of a stent at a target site causes this approach to be not optimum for treatment of coronary lesions and similar stenotic disease states.

It may therefore be desirable to provide systems and methods for delivering a stent to a body lumen that avoid one or more of the aforesaid problems.

SUMMARY OF INVENTION

In accordance with various aspects of the disclosure, a method for delivering a stent to a target region of a body lumen may include positioning a stent delivery system at the target region of a body lumen, the delivery system comprising a stent associated with a catheter and a sheath maintaining the stent in an undeployed configuration; inflating a first balloon portion to a first pressure so as to cause the sheath to split at a first region of the sheath, the first balloon portion being associated with the catheter proximate a first region of the stent, said splitting of the first region of the sheath permitting the first region of the stent to expand to a deployed configuration; preventing propagation of the split from the first region of the sheath to a second region of the sheath at the first pressure with a split-stopping structure of the sheath, said split-stopping structure being between the first and second regions of the sheath; and inflating a second balloon portion to a second pressure so as to cause the sheath to split at the second region of the sheath, the second pressure being greater than the first pressure and the first pressure being insufficient to cause the second region of the sheath to split, the second balloon portion being associated with the catheter proximate a second region of the stent, said splitting of the second region of the sheath permitting the second region of the stent to expand to a deployed configuration. The first part of the deployment can be used as a visual, tactile aid in final positioning of the stent or even in a physical lock with the vessel before final deployment.

According to various aspects of the disclosure, a stent delivery system configured to deliver a stent to a target region of a body lumen may include a catheter; a stent associated with the catheter, the stent having a first region and a second region; a balloon associated with the catheter, the balloon having a first balloon portion associated with the catheter proximate the first region of the stent and a second balloon portion associated with the catheter proximate the second region of the stent; and a sheath about the stent and the balloon, the sheath maintaining the stent in an undeployed configuration for delivery to a target region of a body lumen. The sheath may comprise a first sheath region configured to split at a first pressure thereby permitting the first region of the stent to assume a deployed configuration, a second sheath region configured to split at a second pressure thereby permitting the second region of the stent to assume a deployed configuration, the second pressure being greater than the first pressure and the first pressure being insufficient to cause the second region of the sheath to split, a split-stopping structure between the first and second sheath regions, the split-stopping structure being configured to prevent a split from propagating from the first sheath region to the second sheath region at the first pressure.

BRIEF DESCRIPTION OF THE DRAWINGS

In the drawings:

FIG. 1 shows a diagrammatic view of an exemplary stent delivery system according to various aspects of the disclosure;

FIG. 2 shows a cross-section view of the stent delivery system of FIG. 1.

FIG. 3 shows a diagrammatic view of the stent delivery system of FIG. 1 having an alternate exemplary split-stopping structure;

DETAILED DESCRIPTION

Figure 4:
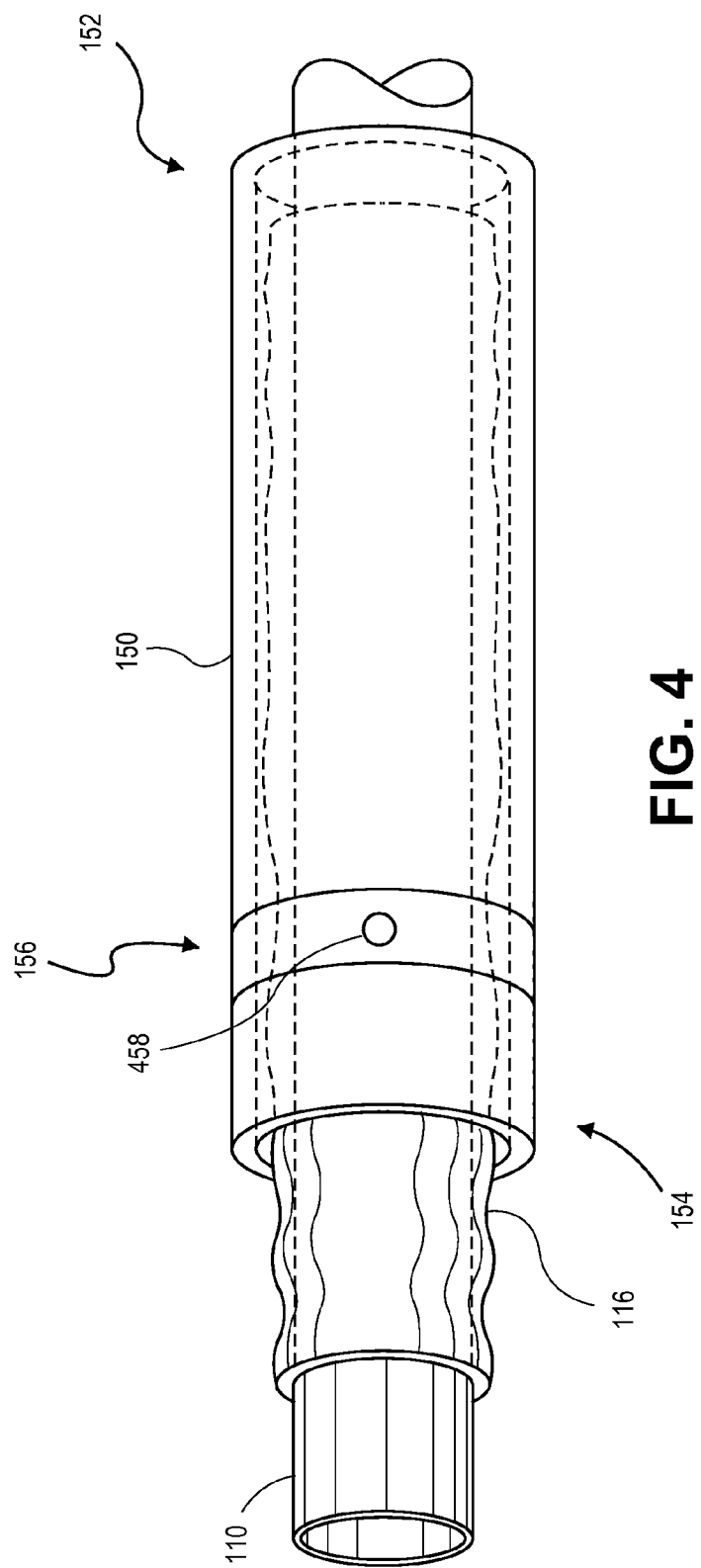
FIG. 4 shows a diagrammatic view of the stent delivery system of FIG. 1 having an alternate exemplary split-stopping structure.

In the following detailed description, numerous specific details are set forth in order to provide a thorough understanding of the invention. It will be understood by those of ordinary skill in the art that the present invention may be practiced without these specific details. In other instances, well-known methods, procedures, components and structures may not have been described in detail so as not to obscure the present invention.

Embodiments of the invention may include an intraluminal device configured to selectively protect at least part of a predetermined region, e.g., an ostial region, of a bifurcated vessel and/or to dispense medication substantially uniformly across at least part of the predetermined region, as described below.

It is to be understood that the present invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is further appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Reference is now made to FIGS. 1 and 2, which schematically illustrates an exemplary delivery system 100 in accordance with various aspects of the disclosure. The stent delivery system 100 may include a catheter 110 having a proximal end 112 and a distal end 114. The catheter 110 may include a balloon 116 at the distal end 114, and a stent 120 associated with the catheter 110 about the balloon 116. The stent 120 may comprise a self-expanding stent having a proximal end 122 and a distal end 124.

The delivery system 100 may include a sheath 150 disposed about the stent 120 and the balloon 116. For example, the stent 120 may be loaded on the catheter between the balloon 116 and the sheath 150 by any known method. The sheath 150 has a proximal end 152 and a distal end 154 and a middle region 156 therebetween. In some aspects, the proximal end 152 of the sheath 150 may be coupled to the catheter 110 for eventual withdrawal of the delivery system 100 from a patient's body lumen. For example, the proximal end 152 of the sheath 150 a desired distance from the proximal end 122 of the stent 120, which distance may in some aspects be about 15 mm. In such a situation, the sheath 150 also includes a proximal region 157 proximate the proximal end 122 of the stent 120, and either the distal end 154 or the proximal region 157 of the sheath 150 may be configured to split at a first pressure, while the other of the proximal region 157 and distal end 154 may be configured to split at a second pressure. According to some aspects, the second pressure is greater than the first pressure by a measurable amount. Various arrangements for effectuating the aforementioned two-stage splitting of the sheath 150, and thus two-stage deployment of the stent 120, are discussed in greater detail below.

It should be appreciated that in some aspects (not shown), the distal end 154 of the sheath 150 may be coupled to the catheter 110, in which case, the distal end 154 may extend distally a desired distance from the distal end 124 of the stent 120. Similar to the aforementioned embodiment, in this alternative embodiment, the sheath 150 would include a distal region proximate the distal end 124 of the stent 120. The distal region would be configured to split at a desired pressure to permit expansion the distal end 124 of the stent 120.

Referring again to FIGS. 1 and 2, the sheath 150 is sized and arranged such that when the sheath 150 is positioned about the stent 120 for delivery to the ostial region of a patient's cardiovascular system, the sheath 150 maintains the stent 120 in an undeployed configuration. The stent 120 is configured such that, upon splitting of the proximal region 157 of the sheath 150, the proximal end 122 of the stent 120 is permitted to assume, for example, via self-expansion, a deployed configuration. Also, upon splitting of the distal end of 154 of the sheath 150, the distal end 124 of the stent 120 is permitted to assume, for example, via self-expansion, a deployed configuration. According to various aspects, the deployed configuration of the stent 120 may comprise an unconstrained configuration where the stent 120 has a substantially cylindrical geometry along substantially its entire length. In some aspects, the deployed configuration of the stent 120 may comprise an unconstrained configuration where the proximal end 122 of the stent 120 has a flared geometry and the distal end 124 of the stent 120 has a substantially cylindrical geometry.

The middle region 156 includes a split-stopping structure 158. The split-stopping structure 158 is configured to prevent a split from propagating from the proximal region 157 of the sheath 150 to the distal end 154 of the sheath 150 or from the distal end 154 of the sheath 150 to the proximal region 157 of the sheath 150. For example, according to some aspects, the proximal region 157 of the sheath 150 may be configured to split at a first pressure, and the distal end 154 of the sheath may be configured to split at a second pressure, which is greater than the first pressure. The split-stopping structure 158 may be configured to prevent the split from propagating from the proximal region 157 of the sheath 150 to the distal end 154 at the first pressure. In some aspects, the split-stopping structure 158 may permit the split to propagate from the proximal region 157 of the sheath 150 to the distal end 154 at about the second pressure. In some aspects, the split-stopping structure 158 may be configured to prevent the split from propagating through the split-stopping structure 158 until a third pressure is applied, wherein the third pressure is greater than the second pressure. Of course, in some aspects, the distal end 154 of the sheath 150 may be configured to split at the first pressure, and the proximal region 157 of the sheath 150 may be configured to split at the second pressure.

Referring to FIG. 3, according to various aspects of the disclosure, the split-stopping structure 158 may comprise a thickened circumferential band 358 extending about the sheath 150. The thickened band 358 may be formed in various manners. For example, the sheath 150 may be initially formed (e.g., by molding or the like) with the thickened band 358, or the thickened band 358 may be formed by heating the initially unthickened middle region 156 of the sheath 150. In some aspects, the sheath 150 may be formed from two separate structures that are butted together or overlapped at the middle region and sealed together in a manner that creates the thickened band 358. Of course, any conventional manner for forming a thickened circumferential band about a middle region of the sheath 150 is contemplated by this disclosure.

Referring again to FIG. 1, the split-stopping structure 158 may comprise a region of the sheath 150 where the longitudinal orientation of the polymer of the sheath is removed or significantly reduced such that a splitting of the sheath 150 from either side of the structure 158 will not propagate through the structure without an application of increased pressure on the region of the sheath to be split. According to various aspects, the longitudinal orientation of the polymer may be removed or significantly reduced by heating. In some aspects, the heating may form a thickened band, as discussed above. In some aspects, no thickened band is formed. According to various aspects, the split-stopping structure 158 may comprise a region extending about 2 mm to 5 mm in the longitudinal direction.

Referring again to FIG. 3, according to some exemplary aspects, the thickened band 358 may have a longitudinal dimension of about 0.2 mm to 1 mm. In aspects where heating the middle region 156 of the sheath 150 removes/reduces the polymer orientation, the region of removed/reduced polymer orientation may extend in the longitudinal direction approximately 1 mm to 2 mm from each side of the thickened band 358.

Referring now to FIG. 4, in some aspects, the split-stopping structure 158 may comprise a pre-formed cutout 468 at the middle region 156 of the sheath 150. Similar to the aforementioned embodiments, the mechanical properties of the cutout 468 will prevent a splitting of the sheath 150 from either side of the cutout 458 from propagating through the cutout 458 without an application of increased pressure on the region of the sheath to be split.

Figure 5:
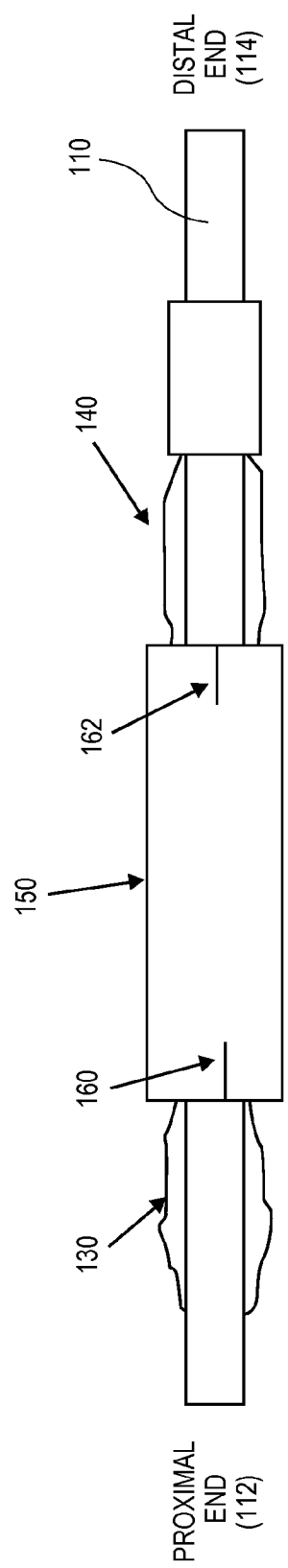
FIG. 5 shows a diagrammatic view of an exemplary stent delivery system according to various aspects of the disclosure.

Referring now to FIG. 5, two-stage splitting of the sheath 150, and thus two-stage deployment of the stent 120, may be effectuated without a split-stopping structure of the sheath. Instead, the balloon 116 may include a first balloon portion 130 proximate the proximal end 122 of the stent 120 and a second balloon portion 140 proximate the distal end 124 of the stent 120. According to various aspects, the first balloon portion 130 is configured to inflate at a first pressure and the second balloon portion 140 is configured to inflate at a second pressure. For example, the balloon 116 may have different compliances at the first and second balloon portions 130, 140 to cause inflation of the first and second balloon portions 130, 140 at different pressures.

In some aspects, the second inflation pressure is greater than the first inflation pressure. For example, the first balloon portion 130 may be inflatable at about 3 to 5 atmospheres, while the second balloon portion 140 may be inflatable at about 12-16 atmospheres. Of course, other inflation pressures are contemplated by this disclosure.

It should be appreciated that, in some aspects, the first balloon portion 130 may be proximate the distal end 124 of the stent 120 and the second balloon portion 140 may be proximate the proximal end 122 of the stent 120. Thus, where the second inflation pressure is greater than the first inflation pressure, the distal end 124 of the stent 120 would be deployed before the proximal end 122.

It should be appreciated that, in some aspects, the first balloon portion 130 and the second balloon portion 140 may comprise a single balloon structure. In some aspects, the first balloon portion 130 and the second balloon portion 140 may comprise separate structures. Each of the first and second balloon portions 130, 140 may have its own inflating assembly or they may share a common inflating assembly.

According to various aspects of the disclosure, the dual-pressure balloon inflation embodiment described in connection with FIG. 5 can used in combination with any one of the split-stopping structures 158 described in connection with FIGS. 1, 3, and 4. Thus, the sheath 150 can be split on one longitudinal side of the split-stopping structure 158 by inflation of the first balloon portion 130 at the first pressure. The split-stopping structure 158 can prevent propagation of the split through the split-stopping structure 158 to the opposite side. Eventual inflation of the second balloon portion 140 to the second pressure can split the opposite side of the split-stopping structure 158 and possibly the split-stopping structure itself.

According to various aspects, the sheath 150 of any one of the aforementioned embodiments may include a pre-formed slit 160 at its proximal end 152, a pre-formed slit 162 at its distal end 154, or both. For simplicity, the slits 160, 162 are only shown in FIG. 5. The slits 160, 162 may be configured to facilitate splitting of the corresponding region of the sheath 150 at a desired pressure or desired pressure.

For example, in some aspects, only the proximal end 152 of the sheath 150 may include the slit 160. When the first balloon portion 130 is inflated to the first pressure, the sheath 150 is configured to split along the slit 160 beginning at the proximal end 152 of the sheath 150 and continuing to split distally until the split reaches the split-stopping structure 158 of the sheath 150.

In some aspects, only the distal end 154 of the sheath 150 may include the slit 162. When the first balloon portion 130 is inflated to the first pressure, the sheath 150 is configured to split along the slit 162 beginning at the distal end 154 of the sheath 150 and continuing to split proximally until the split reaches the split-stopping structure 158 of the sheath 150.

According to some aspects, the proximal end 152 of the sheath 150 may include the slit 160 and the distal end 154 of the sheath 150 may include the slit 162. When the first balloon portion 130 is inflated to the first pressure, the sheath 150 is configured to split along the slit 160 beginning at the proximal end 152 of the sheath 150 and continuing to split distally until the split reaches the split-stopping structure 158 of the sheath 150. Then, when the second balloon portion 140 is inflated to the second pressure, the sheath 150 is configured to split along the second slit 162 beginning at the distal end 154 of the sheath 150 and continuing to split proximally until the split reaches the split-stopping structure 158 of the sheath 150 or the split may propagate through the split-stopping structure 158. Of course, in some aspects, the distal end 154 of the sheath 150 may include the slit 160 and the proximal end 152 of the sheath 150 may include the second slit 162 such that the distal end 154 splits at the first pressure and the proximal end 152 splits at the second pressure.

In some exemplary uses, the delivery system 100 including the catheter 110, the stent 120, and the sheath 150 are delivered to target region of a patient's body lumen. The sheath 150 maintains the stent 120 in an undeployed configuration. The first balloon portion 130 is inflated to the first pressure thereby causing the proximal end 152 of the sheath 150 to split, thus permitting the proximal end 122 of the stent 120 to expand to a deployed configuration. The split is prevented from propagating from the proximal end 152 of the sheath 150 to the distal end 154 of the sheath 150 by the split-stopping structure 158 at the middle region 156 of the sheath 150. The second balloon portion 140 is inflated to the second pressure thereby causing the distal end 154 of the sheath 150 to split, thus permitting the distal end 124 of the stent 120 to expand to a deployed configuration.

In some exemplary uses, the delivery system 100 including the catheter 110, the stent 120, and the sheath 150 are delivered to a target region of a patient's body lumen, while the sheath 150 maintains the stent 120 in an undeployed configuration. The first balloon portion 130 is inflated to the first pressure thereby causing the distal end 154 of the sheath 150 to split, thus permitting the distal end 124 of the stent 120 to expand to a deployed configuration. The split is prevented from propagating from the distal end 154 of the sheath 150 to the proximal end 152 of the sheath 150 by the split-stopping structure 158 at the middle region 156 of the sheath 150. The second balloon portion 140 is inflated to the second pressure thereby causing the proximal end 152 of the sheath 150 to split, thus permitting the proximal end 122 of the stent 120 to expand to a deployed configuration.

In some exemplary uses, the sheath 150 may include a slit 160 at its proximal end 152, its distal end 154, or both so as to facilitate splitting of the respective end of the sheath at a desired pressure. In some exemplary uses, the deployed configuration of the stent may comprise a substantially cylindrical geometry. In some exemplary uses, the deployed configuration of the proximal end 122 of the stent 120 may comprise a flared geometry.

In the case of a delivery system 100 where the stent 140 has proximal end 122 with a deployed configuration comprising a flared geometry, after the proximal end 152 of the sheath is split, the flared proximal end 122 of the stent 120 and the partially-split sheath 150 are then moved distally until the flared proximal end 122 of the stent 120 engages an ostium of the body lumen. With the flared end of the stent engaging the ostium, the second balloon portion 140 is inflated, thereby causing the distal end 124 of the stent 120 to expand to a deployed configuration. Once the stent 120 is deployed, the remainder of the delivery system 100, for example, the catheter 110, the first and second balloon portions 130, 140, and the sheath 150 are removed from the patient's body lumen.

It should be appreciated that a delivery system in accordance with various aspects of the disclosure may include two or more split-stopping structures, thus delimiting multiple regions of a sheath. In such aspects, the multiple regions can be split in multiple stages and the split-stopping structures can prevent the splits from propagating from one region of the sheath into other regions of the sheath until such propagation is desired.

It will be apparent to those skilled in the art that various modifications and variations can be made to the systems and methods for delivering a stent to a body lumen of the present disclosure without departing from the scope of the invention. Other embodiments of the invention will be apparent to those skilled in the art from consideration of the specification and practice of the invention disclosed herein. It is intended that the specification and examples be considered as exemplary only.

What is claimed is:

1. Method for delivering a stent to a target region of a body lumen, the method comprising:
    positioning a stent delivery system at the target region of the body lumen, the delivery system comprising a stent associated with a balloon catheter and a sheath maintaining the stent in an undeployed configuration;
    inflating a first balloon portion to a first pressure so as to cause the sheath to split at a first region of the sheath, the first balloon portion being proximate a first region of the stent, said splitting of the first region of the sheath permitting the first region of the stent to expand to a deployed configuration;
    preventing propagation of the split from the first region of the sheath to a second region of the sheath at the first pressure with a split-stopping structure of the sheath, said split-stopping structure being between the first and second regions of the sheath; and
    inflating a second balloon portion to a second pressure so as to cause the sheath to split at the second region of the sheath until the split at the second region of the sheath reaches the split-stopping structure of the sheath, the second pressure being greater than the first pressure and the first pressure being insufficient to cause the second region of the sheath to split, the second balloon portion being proximate a second region of the stent, said splitting of the second region of the sheath permitting the second region of the stent to expand to a deployed configuration.

2. The method of claim 1, wherein the step of inflating the first balloon portion causes a proximal end of the sheath to split.

3. The method of claim 2, wherein the proximal end of the sheath splits along a pre-formed slit.

4. The method of claim 1, wherein the step of inflating the first balloon portion causes a distal end of the sheath to split.

5. The method of claim 4, wherein the distal end of the sheath splits along a pre-formed slit.

6. The method of claim 1, wherein said first balloon portion has at least one of greater compliance and greater diameter relative to the second balloon portion.

7. The method of claim 6, wherein the first and second balloon portions comprise separate balloons.

8. The method of claim 7, wherein the first balloon portion and the second balloon portion each has its own inflating assembly.

9. The method of claim 6, wherein the first balloon portion and the second balloon portion comprise a single balloon structure.

10. The method of claim 1, further comprising removing the catheter and the sheath from the body lumen.

11. A stent delivery system configured to deliver a stent to a target region of a body lumen, the system comprising:
a catheter, the catheter including a balloon at its distal end;
a stent associated with the catheter about the balloon, the stent having a first region and a second region; and
a sheath about the stent and the balloon, the sheath maintaining the stent in an undeployed configuration for delivery to a target region of a body lumen, the sheath comprising
a first sheath region configured to split at a first pressure thereby permitting the first region of the stent to assume a deployed configuration,
a second sheath region configured to split at a second pressure thereby permitting the second region of the stent to assume a deployed configuration, the second pressure being greater than the first pressure and the first pressure being insufficient to cause the second region of the sheath to split, and
a split-stopping structure between the first and second sheath regions, the split-stopping structure being configured to prevent a split from propagating from the first sheath region to the second sheath region at the first pressure, the split-stopping structure comprising a region having a modified orientation of polymer molecules relative to the first and second sheath regions.

12. The system of claim 11, wherein the balloon has a first balloon portion proximate the first region of the stent and a second balloon portion proximate the second region of the stent.

13. The system of claim 12, wherein the first balloon portion is configured to inflate at the first pressure and the second balloon portion is configured to inflate at the second pressure, the second pressure being greater than the first pressure.

14. The system of claim 12, wherein said first balloon portion has at least one of greater compliance and greater diameter relative to the second balloon portion.

15. The system of claim 14, wherein the first and second balloon portions comprise separate balloons.

16. The system of claim 15, wherein the first balloon portion and the second balloon portion each has its own inflating assembly.

17. The system of claim 14, wherein the first balloon portion and the second balloon portion comprise a single balloon.

18. The system of claim 12, wherein the first sheath region comprises a proximal end of the sheath configured to split distally when the first balloon portion is inflated to the first pressure until the split reaches the split-stopping structure of the sheath.

19. The system of claim 18, wherein the second sheath region comprises a distal end of the sheath configured to split proximally when the second balloon portion is inflated to the second pressure at least until the split reaches the split-stopping structure of the sheath.

20. The system of claim 12, wherein the first sheath region comprises a distal end of the sheath being configured to split proximally when the first balloon portion is inflated until the split reaches the split-stopping structure of the sheath.

21. The system of claim 20, wherein the second sheath region comprises a proximal end of the sheath configured to split distally when the second balloon portion is inflated to the second pressure at least until the split reaches the split-stopping structure of the sheath.

22. The system of claim 11, wherein the split-stopping structure comprises a pre-formed aperture in the sheath.

23. The system of claim 11, wherein the split-stopping structure comprises a circumferential band having a thickened cross-section.

24. The system of claim 11, wherein the catheter and the sheath are configured to be removed from a patient's cardiovascular system after the stent achieves a deployed configuration.

25. The system of claim 11, wherein the difference between the second pressure and the first pressure is a measurable difference.

26. The system of claim 25, wherein the difference between the second pressure and the first pressure is at least 1 atmosphere.

27. The system of claim 11, wherein the first pressure is about 3 to 4 atmospheres, and the second pressure is about 8 to 10 atmospheres.

28. The system of claim 11, wherein at least one of the first region of the sheath and the second region of the sheath has a pre-formed slit.

29. The system of claim 11, wherein a deployed configuration of the stent comprises the first region of the stent having a flared geometry and the second region of the stent having a substantially cylindrical geometry.

* * * * *